US006538113B1

(12) United States Patent
Pelzer et al.

(10) Patent No.: US 6,538,113 B1
(45) Date of Patent: Mar. 25, 2003

(54) METHODS OF OBTAINING ANTIBODY DIRECTED AGAINST PROTHROMBIN FRAGMENTS $F_2/F_{1+2}$

(75) Inventors: Hermann Pelzer, Cölbe (DE); Werner Stüber, Lahntal (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/475,828

(22) Filed: Jun. 7, 1995

Related U.S. Application Data

(62) Division of application No. 07/794,495, filed on Nov. 20, 1991, which is a division of application No. 07/234,121, filed on Aug. 17, 1988, now Pat. No. 5,071,954.

(30) Foreign Application Priority Data

Aug. 19, 1987 (DE) .......................................... 37 27 610

(51) Int. Cl.⁷ .............................................. C07K 16/00
(52) U.S. Cl. .............................. 530/388.25; 530/387.1; 530/389.3
(58) Field of Search ........................... 424/139.1, 152.1, 424/156.1, 158.1, 172.1, 185.1, 94.64, 530; 514/2; 435/70.21, 172.2, 240.3; 530/324, 380, 384, 387.1, 388.25, 388.7, 389.3, 390.5

(56) References Cited

U.S. PATENT DOCUMENTS

| | | | |
|---|---|---|---|
| 4,287,180 A | 9/1981 | Thomas | 424/101 |
| 4,289,498 A | 9/1981 | Baughman et al. | 23/230 |
| 4,334,018 A | 6/1982 | Kirchhof | 435/13 |
| 4,357,321 A | 11/1982 | Thomas | 424/101 |
| 4,459,288 A | 7/1984 | Thomas | 424/101 |
| 4,465,623 A | 8/1984 | Chanas et al. | 260/112 |
| 4,663,164 A | 5/1987 | Thomas | 424/101 |
| 4,668,621 A | 5/1987 | Doellgast | 435/13 |
| 4,769,320 A * | 9/1988 | Furie et al. | 435/7 |
| 5,071,954 A | 12/1991 | Pelzer | 530/324 |

FOREIGN PATENT DOCUMENTS

| | | |
|---|---|---|
| EP | 0 151 239 | 8/1985 |
| WO | WO91/06861 | 5/1991 |

OTHER PUBLICATIONS

Boisclair et al Thromb and Haemostasis vol. 70(2) 253–258, 1993.*
Degen et al, Biochemistry vol. 22 2087–2097, 1983.*
Shi et al, Thromb Haemostasis vol. 62 p. 165 Abstract #493, 1989.*
Bruhn et al Thromb and Haemostasis vol. 68(4) 413–417, Oct. 1992.*
Lerner 1982; Nature vol. 299: 592–596.*
Marglin et al 1970; Ann Rev. Biochem vol. 39: 841–866.*
Walz et al 1977; Proc. Natl. Acad.Sci. USA vol. 74 : 1969–1972.*
Friezner et al 1983; Biochemistry vol. 22: 2087–2097.*
Macqillivray et al 1984; Biochemistry vol. 23 : 1626–1634.*
Ikeda et al., Thrombosis Research, *A Radioimmundassay for Protein C*, 39(3): 297–306 (1985).
Kuyas et al., *Synthetic Peptides for Production of Domain Specific Antibodies*, 34: 197–200 (1986).
Textbook of Immunology, 3rd Edition, James T. Barrett, The C.V. Mosley Co., pp. 72–75 (1978).
Bezeaud et al., British J. Haematology, 58:597–606 (1984).
Bidart et al., J. Immunology, 134:457–464 (1985).
Friguet et al., J. Immunological Methods, 77:305–319 (1985).
Hui et al., Science, 222:1129–1132 (1983).
Advances in Immunology, vol. 36, Frank J. Dixon, ed., Academic Press, Inc., pp. 1–44 (1984).
Moriarty et al., Science, 227:429–433 (1985).
Muller–Berghaus et al., Scand. J. Clin. Lab. Invest., 45, Suppl.178:145–151 (1985).
Niman et al., Proc. Natl. Acad. Sci. USA, 80:4949–4953 (1983).
Pacella, Jr. et al., Molecular Immunology 20:521–527 (1983).
Scheefers–Borchel et al., Proc. Natl. Acad. Sci. USA, 82:7091–7095 (1985).
Teitel et al., Blood, 59:1086–1097 (1982).
Walter et al., Proc. Natl. Acad. Sci. USA, 77:5197–5200 (1980).

(List continued on next page.)

Primary Examiner—Sheela Huff
(74) Attorney, Agent, or Firm—Edwards & Angell, LLP

(57) ABSTRACT

The invention relates to synthetic peptides which have amino acid sequences which correspond, in whole or in part, to the amino acid sequence of prothrombin and are antigenic, to the use thereof for the immunization of an animal and for the purification of specific antibodies, to antibodies against these peptides, and to the use of the antibodies for the determination of the fragments $F_2/F_{1+2}$. The antibodies hitherto used for the determination of the content of the fragments $F_2/F_{1+2}$ have been induced by immunization with natural, highly purified prothrombin fragments $F_2/F_{1+2}$. The isolation of these prothrombin fragments is elaborate and costly, and the antibodies generated therewith show cross-reactions with intact prothrombin. Used for the immunization according to the invention are synthetic peptides which have amino acid sequences which correspond, in whole or in part, to the amino acid sequence of prothrombin and are antigenic. The resulting antibodies react specifically with the antigen used for the immunization; if the peptides contain the carboxyl-terminal amino acid sequence of the fragments $F_2/F_{1+2}$ resulting after cleavage of the prothrombin molecule with factor Xa, then the antibodies generated react specifically with the fragments $F_2/F_{1+2}$ but not with intact natural prothrombin, so that information can be gained about the degree of activation of prothrombin.

21 Claims, No Drawings

OTHER PUBLICATIONS

Walter et al., J. Cell. Biochem., 19:119–125 (1982).

Pelzer et al., Behring Inst. Mitt., 79:80–86 (1986).

White et al., Principles of Biochemistry, 6th Ed., McGraw–Hill Book Co., p. 923.

Pollock et al., J. Biol. Chem., pp. 14216–14223 (Oct. 5, 1988).

Welsch et al., Biochemistry, 27:7513–7519 (1988).

Lau et al., J. Biol. Chem., 254(18):8751–8761 (1979).

Voller et al., "Enzyme–Linked Immunosorbent Assay", in Manual of Clinical Laboratory Immunology, pp. 99–109 (1986).

Gernot Walter et al., "Antibodies specific for the polyoma virus middle–size tumor antigen," Proc. Natl. Acad. Sci. USA, vol. 78, No. 8, pp. 4882–4886, Aug. 1981.

J. Gregor Sutcliffe et al., "Antibodies That React with Predetermined Sites on Proteins," Science, vol. 219, No. 4585, pp. 660–666, Feb. 11, 1983.

Gernot Water, "Production and use of antibodies against synthetic peptides," Journal of Immunological Methods, 88, pp. 149–161, (1986).

Brian S. Schaffhausen, "Designing and Using Site–Specific Antibodies to Synthetic Peptides," Chapter 21, Plenum Press, New York (1985).

Marcie J. Hursting et al., "Monoclonal Antibodies Specific for Prothrombin Fragment 1.2 and Their Use in a Quantitative Enzyme–Linked Immunosorbent Assay," Clinical Chemstry, vol. 39, No. 4, pp. 583–591 (1993).

Christopher P. Price, et al. (Editor), "Principles and Practice of Immunoassay: 2 Production and assessment of antibodies, " M Stockton Press, pp. 19–52.

* cited by examiner

METHODS OF OBTAINING ANTIBODY DIRECTED AGAINST PROTHROMBIN FRAGMENTS $F_2/F_{1+2}$

This is a division of application Ser. No. 07/794,495, filed Nov. 20, 1991, which is a division of application Ser. No. 07/234,121 filed Aug. 17, 1988, now U.S. Pat. No. 5,071,954.

The invention relates to synthetic peptides, to the use of these peptides for immunizing an animal and for purifying specific antibodies against the said peptides, to antibodies against these peptides, and to the use of these antibodies.

The human organism has two systems, which are in equilibrium, to protect itself both from blood loss and from thromboses: the coagulation system and the fibrinolytic system. The relationship between the two systems ensures that insoluble fibrin polymers are produced initially to stop bleeding and, during would healing, are cleaved again by the lytic progress of fibrinolysis.

Plasmin and thrombin are the key enzymes in both systems. Under physiological conditions, the dynamic equilibrium between the coagulation and the fibrinolysis system is under the control of the thrombolytic activity of plasmin and the thromboplastic activity of thrombin.

Thrombin is a typical serine protease and is synthesized in the form of an inactive precursor, prothrombin. Activation of prothrombin is based on proteolysis by coagulation factor Xa, which represents a central position within the coagulation cascade. Factor X itself has a special function in that it can be activated both by the extrinsic and by the intrinsic coagulation pathway. Activated factor X (factor Xa) activates prothrombin by specific cleavage of the prothrombin molecule at the peptide bonds following the tetrapeptide Ile-Glu-Gly-Arg. This cleavage produces, on the one hand, thrombin and, on the other hand, in equimolar concentration the prothrombin fragment $F_{1+2}$. Since one molecule of thrombin and one molecule of prothrombin fragment $F_{1+2}$ are produced from each prothrombin molecule, cleaved, determination of the prothrombin fragment $F_{1+2}$ in blood or plasma allows a direct conclusion about the coagulation potential, which depends on the thrombin concentration present in blood or plasma.

The quantification of thrombin or the prothrombin fragments $F_2/F_{1+2}$ using radioimmunoassays is known from the state of the art. The antisera required are produced by using the prothrombin fragments $F_2$ and $F_{1+2}$, obtained from purified prothrombin molecules, for immunizing animals. The specific antibodies are concentrated from the resulting crude antisera by purification by immunoadsorption on immobilized prothrombin and the corresponding fragments. These antibody preparations are suitable for the determination of the prothrombin fragments $F_2/F_{1+2}$, but do not enable a complete differentiation between intact uncleaved prothrombin and the prothrombin fragments $F_2/F_{1+2}$ liberated by cleavage. Furthermore, the relatively low specificity of this antibody preparation permits determination of the antigen only by use of radioimmunoassays (RIA) which can be carried out in practice only if the conditions set out in the radiation protection regulations are observed and, for this reason, require relatively great technical elaboration and financial cost. Finally, it is continually necessary to prepare fresh antibodies labeled with radioactive isotopes because the isotope iodine-125 normally used for the radiolabeling of proteins has a half-life of only about 2 months.

Hence the object of the present invention was to provide antigens which result in the production of specific antibodies against the prothrombin fragments $F_2/F_{1+2}$ and thus allow rapid and accurate determination of the content of these fragments in biological fluids.

This object is achieved according to the invention by synthetic peptides which have amino acid sequences which partly correspond to the amino acid sequence of prothrombin and are antigenic.

Thus the invention relates to peptides which have amino acid sequences which partly correspond to the carboxyl-terminal end of the fragments $F_2/F_{1+2}$ resulting from the FXa cleavage of thrombin, and which contain the amino acid sequence H-Gly-Asp-Glu-Glu-Gly-Val-Trp-Cys-Tyr-Val-Ala-Gly-Lys-Pro-Gly-Asp-Phe-Gly-Tyr-Cys-Asp-Leu-Asn-Tyr-Cys-Glu-Glu-Ala-Val-Gln-Glu-Glu-Thr-Gly-Asp-Gly-Leu-Asp-Glu-Asp-Ser-Asp-Glu-Glu-Arg-Ala-Ile-Glu-Gly-Arg-OH, in whole or in part, but at least the four carboxyl-terminal amino acids.

Suitable for the preparation of the peptides according to the invention are conventional methods, for example Merrifield solid-phase peptide synthesis (G. Barany and R. B. Merrifield: "Solid-Phase Peptide Synthesis" in E. Gross and J. Meienhofer: The Peptides, Analysis, Synthesis, Biology, Adademic Press, Inc. 1980) as well as customary synthetic strategies constructing the peptides in the form of soluble peptide segments. The peptide of the structure H-Cys(SH)-Leu-Asp-Glu-Asp-Ser-Asp-Glu-Glu-Arg-Ala-Ile-Glu-Gly-Arg was particularly preferably prepared on the solid phase. The Fmoc group has been used as temporary protective group, and the permanent protective groups used were the O-t-Bu protective group for Asp and Glu, t-Bu for Ser, the Mtr group for Arg and the tert.-butylmercapto group for Cys. The C-terminal amino acids were immobilized via p-alkoxybenzyl ester groups which were bonded to 1% crosslinked polystyrene. The peptides were constructed with repeated elimination of the temporary protective group and condensation of the next, protected amino acid using a condensing agent, preferably a carbodiimide. The peptides were cleaved off the resin by acidolysis with simultaneous deprotection of the side-chain groups. Any sulfhydryl groups to be deprotected are deprotected using tri-n-butylphosphine according to the state of the art. The peptides were purified by ion exchange chromatography, RP-HPLC and gel permeation chromatography. The composition of the peptides was confirmed as correct by amino acid analysis.

The use of synthetic peptides as antigens in the immunization of animals results in the generation of antibodies specifically directed against the hapten exposed in this peptide. Hence the antibodies generated in this way are each specific for a single antibody-binding site of the complete protein from which the peptide sequence has been derived. Compared with the use of the natural, purified prothrombin fragments $F_2/F_{1+2}$, the use of synthetic peptides has two additional profound advantages; synthetic peptides can be prepared on a large scale and in high purity so that the elaborate isolation and purification of the natural prothrombin fragments is avoided. Whereas the purification of synthetic peptides from byproducts of the synthesis is well established, even technically elaborate enrichment and purification processes for natural prothrombin fragments always result in preparations which contain a proportion of undesired peptides which, although not detectable still has antigenic activity.

The peptide prepared according to the invention has an amino acid sequence which corresponds completely or in part to the amino acid sequence of prothrombin and is synthesized by one of the conventional processes for peptide synthesis, for example Merrifield synthesis. The selection of the appropriate sequence entails, where possible, selection of the regions which, due to their location on the protein and/or the antigenicity of the exposed epitope, can be predicted to have a highly antigenic effect. The synthetic peptide then has antigenic activity, so that an immune response is triggered by immunization.

Activated factor X (Xa) cleaves the prothrombin molecule at the recognition sequence Ile-Glu-Gly-Arg. Hitherto this tetrapeptide has been detected only in human and bovine prothrombin. The rarity of this tetrapeptide predisposes it for use as a specific feature of the prothrombin molecule.

Prothrombin is cleaved by activated factor X next to the arginine of the sequence Ile-Glu-Gly-Arg. Thus, factor Xa generates a new carboxyl terminus which contains in the terminal region the two amino acids Glu and Arg which have a very high antigenicity index. Peptides or polypeptides which contain the recognition sequence of the factor Xa cleavage site at the C terminus are particularly well suited for immunization.

It has emerged, surprisingly, that antibodies directed against a peptide or polypeptide which contains at its C-terminal end the sequence of the tetrapeptide of the recognition sequence for the factor Xa protease react specifically and exclusively with the prothrombin fragment which has been cleaved off and not with the intact prothrombin molecule.

The fragment produced by the action of factor Xa on prothrombin and which has the factor Xa recognition sequence at the C terminus has a chain length of 273 amino acids. Suitable for immunization are both the entire polypeptide as well as part-sequences of this peptide which, however, still need to have the factor Xa recognition sequence at the C terminus. A particularly preferred embodiment provides for the use of a tetradecapeptide, for example having the sequence Leu-Asp-Glu-Asp-Ser-Asp-Glu-Glu-Arg-Ala-Ile-Glu-Gly-Arg-OH. The only important point in each case is that the carboxyl terminal sequence of the molecule is exposed and results in the immunization.

Shorter peptides suffice in cases where it is not intended for the peptide to trigger an immune response but it is intended that the only function of this peptide is to be recognized by existing antibodies. An embodiment appropriate for this is based on an octapeptide of the sequence Glu-Glu-Arg-Ala-Ile-Glu-Gly-Arg-OH.

In view of the intended use of the peptides, it is appropriate to introduce amino acids with reactive side groups into the peptides in such a way that they do not affect the structure of the hapten. For this reason, it is expedient to attach to the N terminus cysteine as a further amino acid, the free SH group of which is suitable for coupling via thioethers to many carriers. An example which is preferably provided is the antigen represented by the abovementioned peptide in the form of the pentadecapeptide Cys(SH)-Leu-Asp-Glu-Asp-Ser-Asp-Glu-Glu-Arg-Ala-Ile-Glu-Gly-Arg.

The peptide used for the immunization can be prepared both by customary means by chemical synthesis and by purification of a polypeptide made available by genetic manipulation. A conceivable example would be genetic engineering synthesis of the prothrombin fragment $F_2$ or $F_{1+2}$ in E.coli controlled by a strong promoter, or else the synthesis, by genetic manipulation, of a peptide extending beyond the factor Xa cleavage site or a peptide which is subsequently cleaved in vitro by factor Xa, which is likewise obtained by genetic engineering, which results in accessibility to the desired antigenic carboxyl terminus.

It is worthwhile for peptides which are intended to be used for immunization, or those intended to be employed as an immunoadsorbent, to be coupled to a carrier molecule. Examples of customary carrier molecules which are widely used for bovine serum albumin, ovalbumin and polysaccharides. In a preferred embodiment, the peptide or polypeptide is bound to keyhole limpet hemocyanin.

When the synthetic peptides according to the invention are used as immunoadsorbents, it is advisable to couple to materials suitable for preparing solid matrices. A preferred embodiment provides for the coupling of short peptides, for example the abovementioned octapeptide, to Sepharose which has been activated with cyanogen bromide.

Immunization of suitable animals with carrier-bound peptides results reproducibly in the production of antibodies. A preferred animal species for immunization and obtaining antibodies in this context is the rabbit, because in this case there is a favorable relationship between the blood volume obtainable and the expense of breeding and care.

The immunoglobulin fraction relevant for specific assays can be enriched by customary immunoadsorption methods from an antiserum of this type generated in an animal using synthetic peptides according to the invention. However, it is preferred in this case likewise to use as material for a matrix of this type, which is employed for immunoadsorption, a peptide which is coupled to a carrier and has the same antigenic determinant as the peptide employed for the immunization. The peptide used for the purification by immunoadsorption can moreover be considerably shorter; the only prerequisite for use in purification of the desired antibody by immunoadsorption is that the antigenic determinant formed by this shorter polypeptide is recognized and efficiently bound by the desired antibody.

The peptide used for purification of the antibodies by immunoadsorption can be, for example, an octapeptide, preferably the peptide H-Glu-Glu-Arg-Ala-Ile-Glu-Gly-Arg.

According to the invention, antibodies are induced in the animal system by immunization with synthetic peptides and are purified by immunoadsorption. These antibodies react specifically with the peptides used for the immunization and purification. Depending on the sequence of the peptide used, these antibodies bind either only to the fragments $F_2$ and $F_{1+2}$ or else, if a peptide sequence which is exposed in the natural prothrombin molecule is chosen, to the intact prothrombin molecule.

It is possible, by choosing appropriate peptides as immunoadsorbents, to select antibodies which react specifically with the antigenic determinant of prothrombin which corresponds to the sequence of the factor Xa cleavage site of this molecule; in the preferred case where peptides which have the factor Xa-recognition sequence at the C terminus are used both for the immunization and for the purification by immunoadsorption there is enrichment of antibodies against this sequence, but these do not react with intact natural prothrombin, because the factor Xa cleavage site in the natural prothrombin molecule either is not sufficiently exposed or does not have the higher structure required for recognition as an antigen.

The antibodies obtained according to the invention can be employed for a number of immunoassays with a variety of designs. For this purpose, they are expediently coupled to a solid carrier, but are preferably immobilized by adsorption onto polystyrene tubes. The tubes prepared for the following immunoassays can then be stored, closed air-tight, at 4° C.

The amount of prothrombin fragments $F_2/F_{1+2}$ is determined according to the invention by preincubation of the sample with immobilized antibodies of this type, with the concentration of the fragments $F_2/F_{1+2}$ which are bound by the immobilized antibodies being detected by subsequent incubation with a second antibody. This second antibody must have a property which is measurable, for example the ability to react with or bind a chromogenic substrate.

It is expedient for this second antibody to be coupled to a marker enzyme, preferably peroxidase. However, it is also possible to choose to provide the second antibody either with a fluorescent molecule, for example fluorescein isothiocyanate or else with a radioactive label.

The prothrombin fragments $F_2/F_{1+2}$ can also be determined by simultaneous incubation of the sample, preferably of plasma, and labeled antibodies with the immobilized antibodies. Also possible is a competitive determination method entailing competition of labeled and unlabeled prothrombin fragments $F_2/F_{1+2}$ for the binding site on the immobilized antibodies.

The concentration of prothrombin fragments $F_2/F_{1+2}$ determined in this way provides information on the degree of activation of the prothrombin.

The examples illustrate the invention. The following abbreviations are used in the examples:

| | |
|---|---|
| FPA | fibrinopeptide A |
| ELISA | enzyme immunoassay (enzyme-linked immunosorbent assay) |
| RIA | radioimmunoassay |
| KLH | keyhole limpet hemocyanin |
| PBS | phosphate-buffered saline |
| Tris | tris(hydroxymethyl)aminomethane |
| EDTA | ethylenedinitrilotetraacetic acid |
| OD | absorbance (optical density) |
| Asp | l-aspartic acid |
| Ala | l-alanine |
| Arg | l-arginine |
| Gly | glycine |
| Glu | l-glutamic acid |
| Ile | l-isoleucine |
| Ser | l-serine |
| Cys(SH) | l-cysteine |
| Fmoc | 9-fluorenylmethyloxycarbonyl |
| O-t-Bu | tert.-butyl ester |
| t-Bu | tert.-butyl ether |
| Mtr | 4-methoxy-2,3,6-trimethylphenylsulfonyl |
| DMF | dimethylformamide |
| RP-HPLC | reversed phase high performance liquid chromatography |
| GMBS | gamma-maleimidobutyric acid hydroxysuccinimide ester |

EXAMPLE 1

Preparation of an antigen for the immunization a) Peptide synthesis for the pentadecapeptide H-Cys(SH)-Leu-Asp-Glu-Asp-Ser-Asp-Glu-Glu-Arg-Ala-Ile-Glu-Gly-Arg The peptide was synthesized using a semiautomatic peptide synthesizer. 1 g of Fmoc-Arg (Mtr)-p-alkoxybenzyl ester-resin was deprotected with 15 ml of 20% piperidine/DMF (v/v) and then washed several times with DMF and isopropanol. 1 mmol of Fmoc-Glu (3-fold excess) and 203 mg of HOBt dissolved in 15 ml of DMF were added. 1.1 ml of a 1 M diisopropylcarbodiimide solution (dichloromethane) were added and then the coupling was carried out for 1.5 hours. Excess reagents were removed by washing with DMF and isopropanol. This coupling scheme was maintained up to the N-terminal amino acid. The last amino acid employed was a Boc-protected amino acid. Every coupling step was checked for completeness by a ninhydrin test. 1.06 g of resin were stirred with 2.5 ml of thioanisole, 2.5 ml of ethanedithiol and 15 ml of trifluoroacetic acid at 35° C. for 4 hours and were filtered off. The acidic solution was poured into ether, and the precipitated peptide was filtered off and chromatographed on a Sephadex® G25 column (3×100 cm, 0.5% acetic acid). The peptide pool was lyophilized. Yield: 230 mg of peptide.

b) Deprotection of the sulfhydryl group 70 mg of the peptide were dissolved in 7 ml of trifluoroethanol and 350 μl of water, and the pH was adjusted to 7.3 with N-methylmorpholine. The reaction vessel was flushed with nitrogen, and 40 μl of n-tributylphosphine were added. The mixture was stirred at room temperature for 1 hour and was diluted with 50 ml of water, and the pH was adjusted to 4.0. The aqueous phase was extracted three times with 10 ml of diethyl ether, concentrated to 10 ml and purified on Sephadex® G 25 (3×100 cm; 0.5% acetic acid). Yield: 55 mg of peptide.

c) Preparation of conjugate 30 mg of keyhole limpet hemocyanin were dissolved in 0.05 mM sodium phosphate buffer, pH 8.0, and were activated with 3 mg of GMBS for 1 hour. The protein was chromatographed on a Sephadex® G 50 column (2×30 cm) (0.1 M sodium phosphate; 0.5 mM EDTA, pH 6.0). The protein pool was concentrated to 6 ml and incubated with 30 mg of the peptide containing sulfhydryl groups for 1 hour. Yield after dialysis and lyophilization: 38 mg of peptide conjugate.

EXAMPLE 2

Immunization of rabbits 5 rabbits were immunized with 2 mg of antigen per animal each time for a period of 8 weeks; the peptide-KLH conjugate administrations were given subcutaneously and intravenously. The animals were then exsanguinated, and the resulting crude antisera were pooled and stabilized with preservative. Yield: 850 ml of antiserum.

EXAMPLE 3

Preparation of immunoadsorbents

For the purification of the crude antisera by affinity chromatography, about 20 mg of the octapeptide with the sequence H-Glu-Glu-Arg-Ala-Ile-Glu-Gly-Arg-OH (prepared as in Example 1a) were covalently immobilized on a solid phase. The coupling reaction was carried out with Sepharose activated with cyanogen bromide by a described method (Axen, R. et al., Nature, 214, 1302, 1967). The immunoadsorbent was then in each case washed with phosphate-buffered saline (PBS; 0.15 mol/l, pH 7.2) and acetic acid (0.5 mol/l, pH 2.5). Before use, the adsorbent was equilibrated with 3 times the gel volume of PBS. Yield: about 20 ml of peptide-Sepharose.

The tetradecapeptide prepared as in Example 1 was used in the same way to prepare an immunoadsorbent.

EXAMPLE 4

Isolation of specific antibodies 100 ml of crude antiserum were applied to the octapeptide-Sepharose (1.5×15 cm) equilibrated with PBS, and subsequently washed with PBS until the absorbance at 280 nm was 0.01. This was followed by washing steps with saline (1 mol/l, pH 7.0) and water (pH 7.0), with 3 times the gel volume being used in each case. The antibodies were eluted from the immunoadsorbent with 0.1 mol/l acetic acid (pH 2.5), and the antibody solution was adjusted to pH 7.0 with solid sodium phosphate (0.01 mol/l), concentrated (Amicon membrane) and stored at −70° C. Yield: 35 to 40 mg of antibody.

EXAMPLE 5

Assays of the antibodies obtained by immunoadsorption a) Preparation of antibody-coated tubes The antibodies obtained in Example 4 were diluted with tris buffer solution (0.025 mol/l, pH 7.6) to a concentration of 5 μg/ml and immobilized by adsorption onto polystyrene tubes. 250 μl of antibody solution were incubated in each tube at 20° C. for 20 hours, and then the liquid was removed by aspiration, and the tubes were sealed air-tight and stored at 4° C.

b) Procedure for the enzyme immunoassay (ELISA)

The samples to be assayed (plasma, serum) were diluted 1:1 with incubation buffer (0.01 mol/l tris, 0.01 mol/l EDTA, heparin (2 U/ml), 0.05% Tween, pH 7.6), and 200 μl samples in each tube (see Example 5a) were incubated at 37° C. for 30 min. The incubation solution was then removed, and the tube was washed twice with 500 μl of washing solution each time (0.02 mol/l sodium phosphate, 0.05% Tween, pH 7.6). Then 200 μl of peroxidase-conjugated anti-prothrombin antibodies were added, and the tubes were incubated at 37° C. for 30 min. After removal of the conjugate solution and two washes, 200 μl of substrate/chromogen solution (hydrogen peroxide; o-phenylenediamine) were added, and the tubes were incubated at room temperature. After incubation for ½ an hour, the peroxidase was inactivated with sulfuric acid, and the absorbance of the reaction solution at 492 nm was determined.

The absorbances at 492 nm as a function of the plasma or serum dilution are shown in the table which follows, comparing with the absorbance of a tube without plasma or serum.

TABLE 1

| Dilution | $OD_{492}$/30 min |
|---|---|
| Plasma | |
| 1:10 | 0.13 |
| 1:100 | 0.12 |
| 1:1000 | 0.11 |
| 1:10000 | 0.11 |
| Serum | |
| 1:10 | 3.72 |
| 1:100 | 3.71 |
| 1:1000 | 2.81 |
| 1:10000 | 0.97 |
| Buffer blank | 0.045 | c) Procedure for an enzyme immunoassay (ELISA) for determining fragments $F_2/F_{1+2}$ formed in vitro.

Another experiment was carried out to examine the specificity of the antibodies against the fragments $F_2/F_{1+2}$. Plasma anticoagulated with citrate solution was recalcified with calcium chloride solution (final concentration of calcium chloride: 0.025 mol/l). Aliquots were removed at various times, and the reaction was stopped by addition of EDTA (0.1 mol/l), antithrombin III (3 IU/ml) and heparin (5 IU/ml). The samples were diluted 1:1 with incubation buffer and assayed using the ELISA.

The table shows the results.

TABLE 2

| Time (min) | $OD_{492}$/39 min. |
|---|---|
| 0 | 0.18 |
| 3 | 0.30 |
| 6 | 0.32 |

TABLE 2-continued

| Time (min) | $OD_{492}$/39 min. |
|---|---|
| 12 | 0.58 |
| 15 | 1.20 |
| 18 | 1.69 |
| 21 | 1.88 |
| 25 | 1.96 |
| Buffer blank | 0.045 |

The results show that the fragments $F_2/F_{1+2}$ can be measured quantitatively in this way: the concentration of the fragments $F_2/F_{1+2}$ increases with increasing time during the recalcification reaction.

The peptides according to the invention, which have an amino acid sequence which corresponds, in whole or in part, to the amino acid sequence of prothrombin and is antigenic thus induce binding-specific antibodies against each of the antigenic determinants present in the peptide. These specific antibodies can then be purified by immunoadsorption on peptides having the same antigenic determinants. The use of synthetic peptides has the considerable advantage that absolutely pure antigens are employed for the immunization, so that no cross-reaction whatever with other proteins or other parts of the prothrombin molecule can occur in the resulting immune serum. Preferably used according to the invention is a peptide which contains the factor Xa cleavage site. Using an antibody against this peptide it is possible to detect only cleaved prothrombin molecules, because this sequence is not accessible to antibody recognition in intact natural prothrombin. Measurement of the quantity of bound antibody provides direct information on the concentration of liberated prothrombin fragments $F_2/F_{1+2}$ and thus on the degree of activation of prothrombin.

What is claimed is:

1. A method of obtaining an antibody that specifically binds prothrombin fragments F2/F1.2 and that does not bind intact prothrombin, comprising immunizing an animal with an immunizing peptide that is at least four and less than eight amino acids in length, wherein the carboxyl-terminus of the immunizing peptide ends with the amino acids Ile Glu-Gly-Arg-OH, and wherein said animal produces antibodies after such immunizing, and purifying the antibody that specifically binds prothrombin fragments F2/F1+2 and that does not bind intact prothrombin by immunoadsorbing the antibody to a carrier-bound immunoadsorbing peptide that is at least four and less than eight amino acids in length and that includes the amino acid sequence lle-Glu-Gly-Arg-OH, and recovering the antibody from the carrier bound immunoadsorbing peptide.

2. A method as claimed in claim 1, wherein the immunizing peptide is conjugated to a carrier and the carrier is not conjugated at the carboxy-terminus of the immunizing peptide.

3. A method as claimed in claim 1, wherein the purifying comprises immunoadsorbing the antibody to an immunoadsorbing peptide that has a carboxyl-terminus that ends with the amino acids Ile-Glu-Gly-Arg-OH.

4. A method as claimed in claim 3, wherein the immunizing peptide consists of a different amino acid sequence than the immunoadsorbing peptide.

5. A method as claimed in claim 1, wherein the animal is a rabbit.

6. A method of purifying an antibody that specifically binds F2/F1+2 fragments and that does not bind intact prothrombin, comprising immunoadsorbing the antibody to a carrier-bound immunoadsorbing peptide that is at least four and less than eight amino acids in length wherein the carboxyl-terminus of the immunoadsorbing peptide ends with the amino acids lle-Glu-Gly-Arg-OH, and recovering the antibody from the immunoadsorbing peptide.

7. A method as claimed in claim 3, wherein the immunizing peptide is conjugated to a carrier which carrier is not conjugated at the carboxy-terminus of the immunizing peptide.

8. A method as claimed in claim 3, wherein the immunoadsorbing peptide does not bind to an antibody that binds to prothrombin.

9. A method as claimed in claim 4, wherein the peptide is conjugated to a carrier which carrier is not conjugated at the carboxy-terminus of the immunizing peptide.

10. A method of obtaining an antibody that specifically binds prothrombin fragments F2/F1.2 and that does not bind intact prothrombin, the method comprising immunizing an animal with an immunizing peptide that is at least 4 and less than eight amino acids in length, wherein the carboxyl-terminus of the immunizing peptide ends with the amino acids Ile-Glu-Gly-Arg-OH, and wherein said animal produces antibodies after such immunizing, and purifying the antibody that specifically binds prothrombin fragments F2/F1+2 and that does not bind intact prothrombin by immunoadsorbing the antibody to a carrier-bound immunoadsorbing peptide that is at least 4 and less than 8 amino acids in length and that includes the amino acid sequence lle-Glu-Gly-Arg-OH and recovering the antibody from the carrier bound immunoadsorbing peptide, wherein the immunizing peptide is bound to carrier and the carrier is not bound to the carboxy terminus of the immunizing peptide.

11. The method of claim 10, wherein the immunizing peptide is 4, 5 or 6 amino acids in length.

12. The method of claim 10 or 11, wherein the immunoabsorbing peptide is 4, 5 or 6 amino acids in length.

13. A method of purifying an antibody that specifically binds F2/F1+2 fragments and that does not bind intact prothrombin, the method comprising immunoadsorbing the antibody to a carrier-bound immunoadsorbing peptide that is at least 4 and less than 8 amino acids in length, wherein the carboxyl-terminus of the immunoadsorbing peptide ends with the amino acids lle-Glu-Gly-Arg-OH, and recovering the antibody from the immunoadsorbing peptide.

14. The method of claim 1, 6, 10 or 13, wherein the antibody binds the following peptide sequence as determined by an enzyme immunoassay:

II-Ile-Glu-Gly-Arg-OH,

H-Ala-Ile-Glu-Gly-Arg-OH,

H-Arg-Ala-Ile-Glu-Gly-Arg-OH, or

H-Glu-Arg-Ala-Ile-Glu-Gly-Arg-OH.

15. The method of claim 14, wherein the peptide sequence is bound to a carrier.

16. The method of claim 14, wherein the ELISA immunoassay comprises immobilizing the antibody and contacting the immobilized antibody with a labeled second antibody.

17. The method of claim 16, wherein the labeled second antibody provides an OD/30 min of between from about 0.1 to about 4 in the ELISA immunoassay.

18. A method of purifying an antibody that specifically binds F2/F1+2 fragments and that does not bind intact prothrombin, the method comprising immunoadsorbing the antibody to a carrier-bound immunoadsorbing peptide that is at least 4 amino acids in length, wherein the carboxyl-terminus of the immunoadsorbing peptide ends with the amino acids lle-Glu-Gly-Arg-OH, and recovering the antibody from the immunoadsorbing peptide and further wherein the immunoabsorbing peptide is 4, 5 or 6 amino acids in length.

19. A method of obtaining an antibody that specifically binds prothrombin fragments F2/F1.2 and that does not bind intact prothrombin, comprising immunizing an animal with an immunizing peptide that is 4, 5 or 6 amino acids in length, wherein the carboxyl-terminus of the immunizing peptide ends with the amino acids Ile-Glu-Gly-Arg-OH, and wherein said animal produces antibodies after such immunizing, and purifying the antibody that specifically binds prothrombin fragments F2/F1+2 and that does not bind intact prothrombin by immunoadsorbing the antibody to a carrier-bound immunoadsorbing peptide of 4, 5 or 6 amino acids in length that includes the amino acid sequence lle-Glu-Gly-Arg-OH, and recovering the antibody from the carrier bound immunoadsorbing peptide.

20. A method of purifying an antibody that specifically binds F2/F1+2 fragments and that does not bind intact prothrombin, comprising immunoadsorbing the antibody to a carrier-bound immunoadsorbing peptide that is 4, 5 or 6 amino acids in length, wherein the carboxyl-terminus of the immunoadsorbing peptide ends with the amino acids lle-Glu-Gly-Arg-OH, and recovering the antibody from the immunoadsorbing peptide.

21. A method of obtaining an antibody that specifically binds prothrombin fragments F2/F1.2 and that does not bind intact prothrombin, the method comprising immunizing an animal with an immunizing peptide that is 4, 5, or 6 amino acids in length, wherein the carboxyl-terminus of the immunizing peptide ends with the amino acids Ile Glu-Gly-Arg-OH, and wherein said animal produces antibodies after such immunizing, and purifying the antibody that specifically binds prothrombin fragments F2/F1+2 and that does not bind intact prothrombin by immunoadsorbing the antibody to a carrier-bound immunoadsorbing peptide that includes the amino acid sequence lle-Glu-Gly-Arg-OH and recovering the antibody from the carrier bound immunoadsorbing peptide of 4, 5, or 6 amino acids in length, wherein the immunizing peptide is bound to carrier and the carrier is not bound to the carboxy terminus of the immunizing peptide.

* * * * *